(12) United States Patent
Bain et al.

(10) Patent No.: US 11,906,486 B2
(45) Date of Patent: *Feb. 20, 2024

(54) MATTRESS EVALUATION SYSTEM AND METHOD

(71) Applicant: CHAPELGLADE LIMITED, Dublin (IE)

(72) Inventors: Duncan Bain, Hertfordshire (GB); John Bain, Hertfordshire (GB); David Woolfson, County Dublin (IE)

(73) Assignee: CHAPELGLADE LIMITED, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 18/045,333

(22) Filed: Oct. 10, 2022

(65) Prior Publication Data

US 2023/0057583 A1   Feb. 23, 2023

Related U.S. Application Data

(63) Continuation of application No. 16/302,986, filed as application No. PCT/EP2017/062020 on May 18, 2017, now Pat. No. 11,467,076.

(30) Foreign Application Priority Data

May 19, 2016   (GB) ..................... 1608840

(51) Int. Cl.
*G01N 3/42* (2006.01)
*A47C 31/12* (2006.01)
(Continued)

(52) U.S. Cl.
CPC ............. *G01N 3/42* (2013.01); *A47C 31/123* (2013.01); *G01M 99/001* (2013.01);
(Continued)

(58) Field of Classification Search
CPC ..... A41C 31/123; G01M 99/001; G01N 3/40; G01N 3/42; G01N 2203/0033;
(Continued)

(56) References Cited

U.S. PATENT DOCUMENTS 3,195,347 A   7/1965 Janapol
9,261,354 B1   2/2016 Mercado
(Continued)

FOREIGN PATENT DOCUMENTS

EP   0884559 A2   12/1998
JP   H0814851 A   1/1996
(Continued)

OTHER PUBLICATIONS

Combined Search and Examination Report under Sections 17 and 18(3) dated Sep. 29, 2016, received for British Application No. GB1608840.3.

(Continued)

*Primary Examiner* — Erika J. Villaluna
(74) *Attorney, Agent, or Firm* — Kinney & Lange P.A.

(57) ABSTRACT

A system for simultaneously measuring the indentation hardness properties, span properties, and resilience properties of a mattress includes a first indentation means and a second indentation means, and means for urging the first indentation means and the second indentation means into the mattress with a predetermined force, and also includes laser means for projecting a laser line configured to map, preferably by photographic triangulation, the amplitude, shape, and time-dependency of the resultant deflection of the mattress surface between the first indentation means and the second indentation means. A method for simultaneously measuring the indentation hardness properties, span properties, and resilience properties of a mattress is also provided.

19 Claims, 5 Drawing Sheets

(51) Int. Cl.
*G01M 99/00* (2011.01)
*G01N 3/48* (2006.01)
*G01N 3/06* (2006.01)
*G01N 33/00* (2006.01)

(52) U.S. Cl.
CPC .......... *G01M 99/007* (2013.01); *G01N 3/068* (2013.01); *G01N 3/48* (2013.01); *G01N 2033/0078* (2013.01); *G01N 2203/0033* (2013.01); *G01N 2203/0075* (2013.01); *G01N 2203/0085* (2013.01); *G01N 2203/0647* (2013.01)

(58) Field of Classification Search
CPC .... G01N 2203/0076; G01N 2203/0078; A47C 31/123
See application file for complete search history.

(56) References Cited

U.S. PATENT DOCUMENTS

2006/0144129 A1 7/2006 Farritor et al.
2015/0196132 A1 7/2015 Duffy et al.

FOREIGN PATENT DOCUMENTS

| | | |
|---|---|---|
| WO | 2014012598 A1 | 1/2014 |
| WO | 2014083337 A1 | 6/2014 |
| WO | 2015110639 A1 | 7/2015 |

OTHER PUBLICATIONS

International Search Report and Written Opinion dated Jul. 18, 2017, for corresponding PCT Application No. PCT/EP2017/062020.

MATTRESS EVALUATION SYSTEM AND METHOD

CROSS-REFERENCE TO RELATED APPLICATION(S)

This application is a continuation of U.S. application Ser. No. 16/302,986, filed Nov. 19, 2018, which claims priority to PCT Application No. PCT/EP2017/062020, filed May 18, 2017, which claims priority to United Kingdom Application No. 1608840.3, filed on May 19, 2016, all of which are incorporated herein by reference in their entireties.

TECHNICAL FIELD

The present invention relates to a Mattress Evaluation System and Method. The present invention relates, in particular, to a mattress measuring tool and in particular, to a mattress categorization tool.

BACKGROUND

Mattresses exist in a wide variety of different constructions, with differing support properties. It is desirable to be able to measure and characterize the properties of a mattress for a number of reasons. Firstly, it is advantageous to enable a manufacturer to maintain a consistent product in terms of support properties, including when that manufacturer wishes to produce a mattress using a different construction or different materials. Secondly, it enables a manufacturer to improve mattress design, by giving the capability to verify that certain support characteristics have been achieved. Thirdly, it is desirable to allow the grouping of mattresses with similar characteristics, for the purpose of recommending alternatives or replacements to a consumer.

The present invention seeks to alleviate the disadvantages associated with any known mattress measuring tool. Accordingly, the present invention relates to a mattress measuring tool and in particular, to a mattress categorization tool.

In using the system described in the Applicant's co-pending patent applications derived from PCT Patent Application No. PCT/EP2015/051513, it is important that the mattresses, which may emanate from a number of different manufacturers and be subject to different national and regional regulations, are measured and categorized according to a standardized scheme to allow for accurate and reliable comparison.

As is well known, it is important for individuals to sleep on mattresses which are suited to that individual's body type. Different mattresses have different characteristics and the characteristics of the mattress will affect the quality of sleep which the individual will experience. From research, it has been found that a mattress comprises three important characteristics, namely, support, conformity and resilience (which is the converse of viscosity). These properties have previously been measurable to a crude level of accuracy by methods described in WO2014012598 (A1) Bain DS (Mytronic patent).

Support is essentially the firmness of the mattress itself which ranges from a soft support to a hard/firm support. This may be quantified in terms of the distance deflected under a given force, or in terms of the force required to produce a given deflection.

The conformity characteristic is a measurement of the ability of the mattress to deform around an individual's body, without the neighboring parts of the mattress also deforming and deflecting; it is in essence a measurement of the localization effect of the deflection of the mattress, which is to say, the ability of neighboring parts of a surface of the mattress to deform or deflect, independently of each other.

This property differs from the support property of a mattress (how much the mattress deflects under a given load), since it takes into account the relative movement between adjacent areas of the mattress, rather than simply the overall absolute displacement. It will be understood, in an extreme example, that a rigid steel sheet on top of a very soft sponge will have a soft level of support, since the sheet will displace downwards substantially under load. However, this arrangement will have a very low level of conformity, since there will be very little relative displacement between adjacent regions of the steel sheet.

An additional property related to conformity may be referred to as the 'effective wavelength' or 'span' of a mattress. To explain this property, a number of principles of mattress support must first be understood:

1) When a body is supported by a mattress, the weight of the body acts vertically downwards, according to gravity.

2) For static equilibrium to be maintained, there must be an equal and opposite reaction force, such that all forces, including the body weight, sum to zero.

3) One possible component of the reaction force is direct reaction from the mattress filling. For example, if the mattress has a spring base filling, vertical compression of the springs will be accompanied by a vertical reaction force acting from the springs to the body. In the case of a spring base adhering to Hooke's Law, the reaction force from each spring will be proportional to the vertical compression of each spring. Thus, pressure will not be evenly distributed across the body surface, but will be highest in those regions which indent furthest into the mattress.

4) Another possible component of the reaction force is due to tension in the mattress cover. For example, if a body is lying in a hammock, the entire reaction force is provided by tension in the fabric. Changes in direction of the fabric tension, as the fabric wraps around the body, deliver reaction forces distributed across the body. Thus, pressure will not be evenly distributed across the body surface, but will be highest in those regions which are the most convex.

5) Most practical mattresses have a combination of these two components: compressive (normal) support, and surface tension (circumferential, or 'hammock') support. It should be noted that the surface 'hammock' tension does not necessarily result from the covering material of the mattress, but from any component which provides horizontal/circumferential tension. Certain types of ticking, or elastomer foam in the upper layers, or linked springs, would be typical examples.

It will be understood from 3) and 4) above that the distribution of peak pressures will differ markedly between the two types of support.

It will be further understood that mattresses will vary in terms of how support is apportioned between the component of support provided by direct reaction as in 3) above, and the component of support provided by surface 'hammock' tension as in 4) above.

If the 'hammock' component predominates in the support characteristics of the mattress, a narrow object pushed into the mattress surface will create an indentation in the mattress surface much bigger than the object itself. Traditionally, this 'conformity' characteristic may be tested informally, by pushing a fist into the mattress. In a 'high conformity' mattress, the indentation in the mattress will not be much wider than the fist itself. In a low conformity mattress, a large surrounding area will be displaced, coupled to the first by tension in the mattress cover. This feature, known as conformity, has previously been considered because of its importance in distributing contact over irregular shapes, so reducing peak interface pressures, and improving skin comfort.

We are now, for the first time, considering the postural implications of properties related to hammock tension.

A further implication of increased 'hammock' surface tension is that two shapes indenting into the mattress in close proximity to each other will not be independent of each other. For example, consider a substantial object, such as a heavy cylindrical fire extinguisher, placed upright on the mattress surface, such that it sits balanced in its own indentation. Now consider the effect of placing another heavy cylinder on the mattress 20 cm away from the first cylinder. The indentation caused by the second cylinder will overlap the indentation caused by the first cylinder, increasing the displacement on the near side. This will have the effect of unbalancing the first cylinder. If, instead, we place the second cylinder 50 cm away from the first cylinder, this effect will be lessened. It will be understood that there will be a minimum spacing between cylinders such that no such effect is observed, because the indentations are mutually independent. We shall call this distance the span of the mattress.

This spacing will depend upon the hammock tension, since a mattress with a large hammock component will require the two cylinders to be further apart to maintain independence from each other. Thus, a mattress with a relatively large hammock support component will have a longer span than a mattress with relatively little hammock support component.

Now consider the human body, side-lying on a mattress. The structure may be considered analogous to a suspension bridge: the shoulder girdle constitutes one major support column, indenting into the mattress; the pelvic girdle represents another major support column, indenting into the mattress. The spine is the bridge between the two. For the spine to remain straight and correctly aligned, it is important for the two columns to remain vertical.

Considering the two cylinders previously discussed: this requirement would be met if the two cylinders were spaced at or greater than their minimum span. In the case of the body, the situation is slightly more complicated, since other forces also act on the pelvis and shoulders. The weight of the legs may be considered to be cantilevered on the pelvis, with a tendency to tilt the pelvis away from the shoulders. Similarly, the weight of the head will tend to tilt the shoulders away from the pelvis. The effect of the mid-section will vary, depending on the physique of the individual. Therefore, to adjust and correct for physique, the mattress will have to have a span which is correct for the individual. If the span is too large for the individual (longer than the spacing between the individual's shoulder girdle and pelvic girdle), each structure will interfere with the other, causing them to slope inwards (towards each other), and the spine will sag. If the span is too short for the individual, there will be not enough of this effect to counteract the cantilever effects of the legs and head. This will cause the pelvic girdle and shoulder girdle to slope outwards, and the spine will heave upwards.

For the purposes of matching individual body characteristics to suitable mattress constructions, it is therefore desirable to provide a means of testing the mattress span.

Finally, resilience, is the speed at which a surface of a mattress will recover to its original shape following deflection, when a load causing the deflection has been removed. This has implications on the ease of rolling over or otherwise changing a sleeping position when lying on the mattress, which is an important consideration for certain body types.

It is known from the prior art to measure the support, or hardness, the mattress through various techniques. One such technique involves dropping a weighted ball onto the mattress and observing the rebound height of the weighted ball.

A further example is the Mattress Testing Machine offered by Dongguan Haida Equipment Company Limited which comprises a spherical protrusion at the bottom of a rigid, circular plate which is indented against a mattress and records the force curve and displacement for subsequent analysis. The Mattress Testing Machine comprises a framework having a pair of legs and single mattress-engaging spherical protrusion. It is believed that the Mattress Testing Machine uses a load cell to record the force values. The Mattress Testing Machine only measures support.

There are further examples of machines for measuring the hardness of the mattress, but all of these machines only use a single mattress-engaging element and are not suited for carrying out any other mattress characteristic measurements.

It is a goal of the present invention to provide an apparatus that overcomes at least one of the above mentioned problems but providing a mattress measurement machine which measures a multitude of mattress characteristics, and in particular a mattress categorization tool capable of measuring span, support, conformity and resilience, with a single quick measurement.

SUMMARY

Features of the present invention are set forth in the appended claims and include the features of the following statements:
1. A system for simultaneously measuring the indentation hardness properties, span properties, and resilience properties of a mattress, comprising a first indentation means and a second indentation means, and means for urging the first indentation means and the second indentation means, into the mattress with a predetermined force, and also comprising laser means for projecting a laser line configured to map, the amplitude, shape, and time-dependency of the resultant deflection of the mattress surface between the first indentation means and the second indentation means.
2. A system as in statement 1 wherein the mapping is carried out by photographic triangulation.
3. A system as in statement 1 wherein the first and second indentation means are operable independently of each other.
4. A system as in statement 1 wherein the first and second indentation means are operable together and optionally, are rigidly connected together so as to facilitate simultaneous operation.
5. A method for simultaneously measuring the indentation hardness properties, span properties, and resilience properties of a mattress, comprising the steps of: providing a first indentation means and a second indentation means, and providing means for urging the first indentation means a the second indentation means, independently of each other, into the mattress with a predetermined force, and providing laser means for projecting a laser line while urging the first and second indentation means into the mattress; and providing means for mapping, the amplitude, shape, and time-dependency of the resultant deflection of the mattress surface between the first indentation means and the second indentation means.
6. A method as in statement 5 wherein the mapping is carried out by photographic triangulation.

The present invention will now be described more particularly, by way of example only, with reference to the appended drawings in which are shown, one embodiment of the system of the present invention.

DETAILED DESCRIPTION

Figure 1:
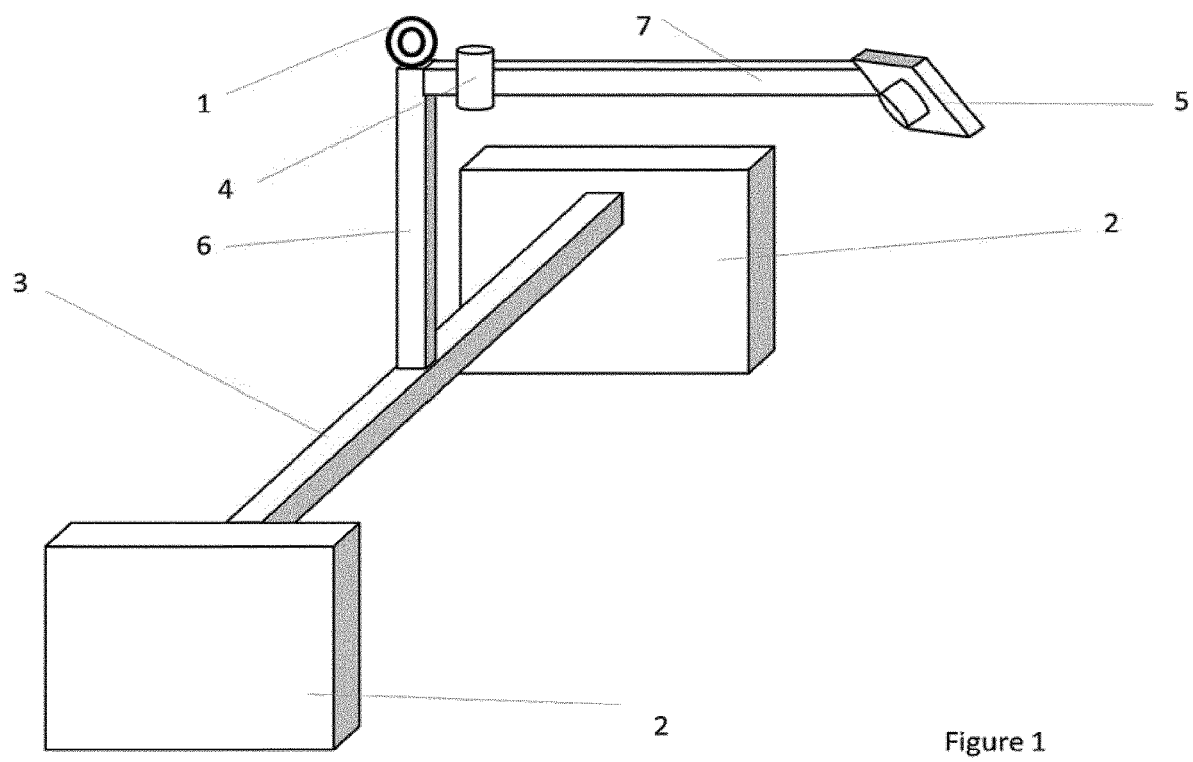
FIG. 1 is a perspective view of the arrangement comprising the first indentation means and second indentation means comprising, respectively, a first weighted means and a second weighted means; and a laser mounted between the first and second indentation means.

Referring to FIG. 1, the system of the present invention comprises first and second indentation means comprising of two heavy masses 2 are rigidly connected by a substantial rigid member 3. The masses preferably comprise a straight edge at their lower surface, and flat faces facing each other, although other geometries will also be practicable. The rigid member 3 is rigidly connected to a vertical member 6, which may be provided with a hoist eye or similar, 1, to allow the assembly to be raised and lowered. Connected to member 6 is a horizontal member 7, aligned at 90 degrees to both 6 and 3. Member 7 serves as a mounting point for a line laser 4 and a camera 5. The laser 4 is of the type which incorporates a lens so that it projects a line on any surface, as opposed to a dot. It is mounted such that it projects a line vertically beneath it, spanning between the masses 2. The camera is mounted horizontally offset from the projection line of the laser, to allow visualization by oblique triangulation of the distance of the surface on which the line is projected. It will be understood that the purpose of the members 3, 6, and 7 is to provide appropriate positions, orientations, and offsets for the laser 4 and camera 5, and exact right angles are not necessary for this purpose. Other configurations will function.

Figure 2:
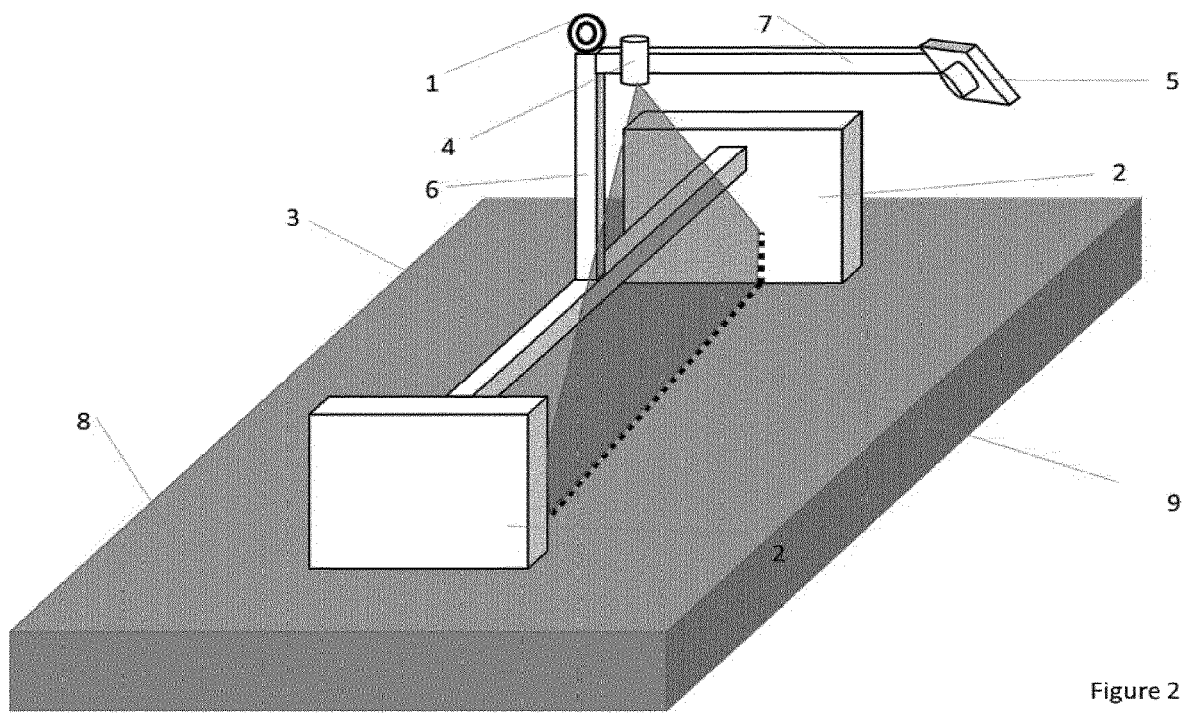
FIG. 2 is a perspective view of the arrangement of FIG. 1 shown ready for use with a mattress.

Referring now to FIG. 2, the assembly is lowered until it makes touching contact with the surface of a mattress 8. The laser line 9 is projected onto the surface of the mattress. Since the surface of the mattress is flat and un-deformed, the line is straight, and will appear so to camera 5.

Figure 3:
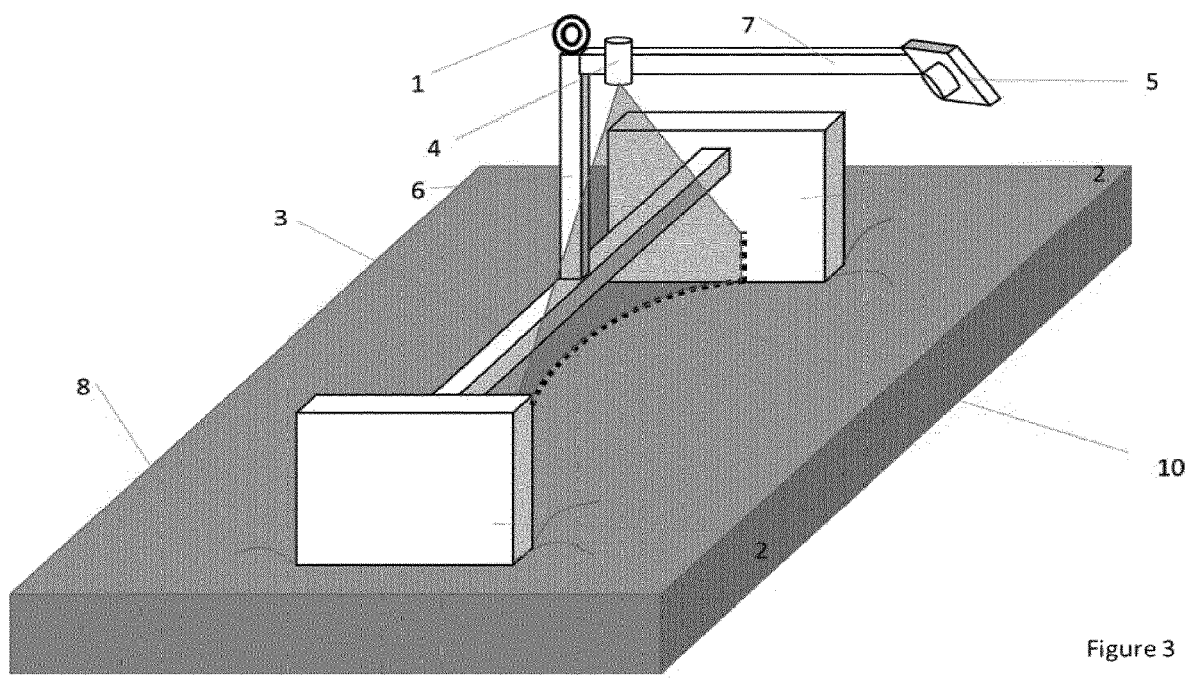
FIG. 3 is a perspective view of the arrangement in FIG. 2 with the first and second indentation means urged into the mattress.

In FIG. 3, the assembly is lowered onto the mattress, so that the full weight of the assembly is now resting on the mattress, causing a corresponding displacement and deformation of the mattress surface. The projected laser line now takes on a curved shape 10, corresponding to the deformed shape of the mattress surface between the two masses.

It will be appreciated that lowering the assembly onto the mattress under its own weight is only one possible method of causing the indentation of the assembly into the mattress under load. Equally, a relatively light assembly could be driven into the mattress with an actuator until the prescribed load or the prescribed deformation was achieved. Many other methods will be obvious to those skilled in the art.

Figure 4:
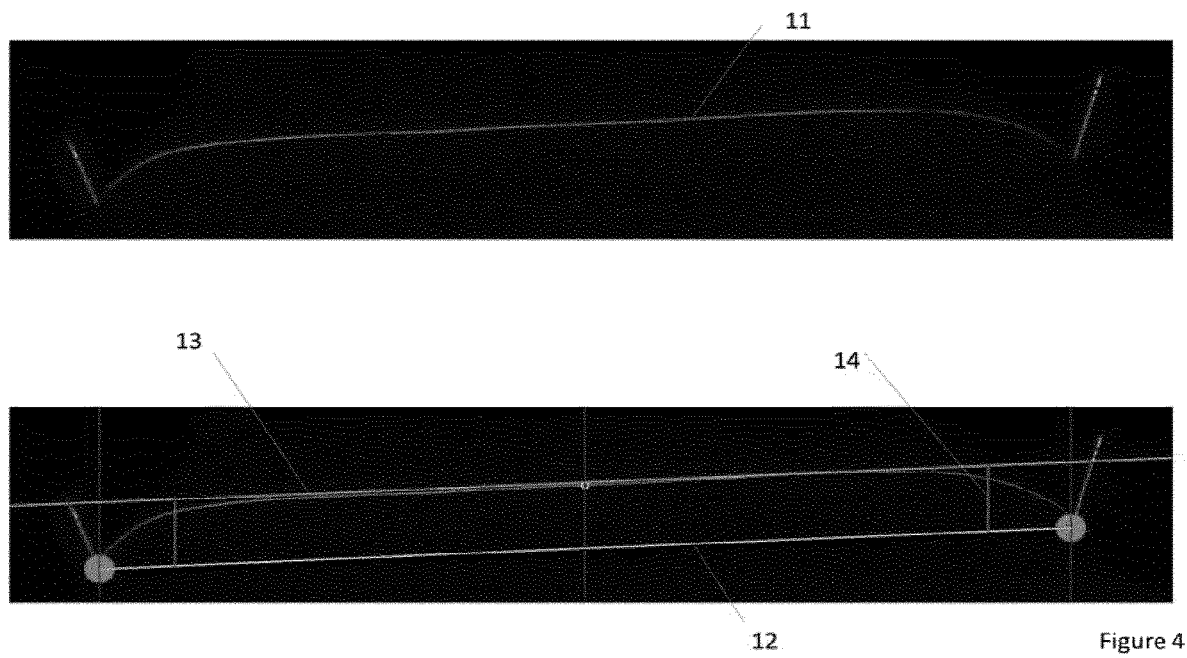
FIG. 4 shows the projected laser line as seen by the camera.

FIG. 4 shows the projected laser line as seen by the camera. The top image shows the laser line 11 distorted from the straight line as it follows the surface of the mattress. The bottom image shows various useful measurements which may be taken from this image.

Firstly, a baseline 12 may be established as the original position of the undeflected laser line. This may be captured on contact, or interpolated between the lower extremities of the masses 2, or otherwise calibrated. This line, now in the loaded condition, indicates the final position of penetration into the mattress of the lower edge of the masses.

Line 13 shows is the maximum vertical displacement of the laser line under load from the baseline 12. The vertical distance between line 13 and line 12 is a functional measure of the softness/firmness of the mattress. An absolute value of displacement is readily calculated by dividing the measured value by the sine of the offset of the camera from the vertical, scaling by the known distance between masses 2, or other calibration means.

The vertical pink lines 14 represent the position on the laser line 11 which approaches the position of the original surface position (represented by the white line 13. In this case, the criterion is recovery to 80% of the distance between lines 12 and 13. This is found to be more robust than 100% (i.e. exactly coincident with 13), since the small gradient of 11 at that point leads to magnified measurement error. However, other proportions (50%, 60%, 90% etc.) may also be used effectively.

Using this line as a marker gives us a measure of the local conformity behavior of the mattress, since it is essentially a measure of the size of the indentation made by the mass 2. In this case, it tells us what distance from mass 2 still experiences 20% displacement due to the displacement of mass 2.

This line can also be used to give a measure of span. For example, by subtracting the section where 11 and 13 coincide from the total distance between masses, we are left with an effective span, i.e. the minimum distance between masses for them to have no influence on each other. Alternatively, span may be calculated from the horizontal spacing of the lines 14, with appropriate corrections. It will be understood that many other methods (e.g. polynomial modelling) are possible for characterizing the indentation profile line provided by the apparatus.

Figure 5:
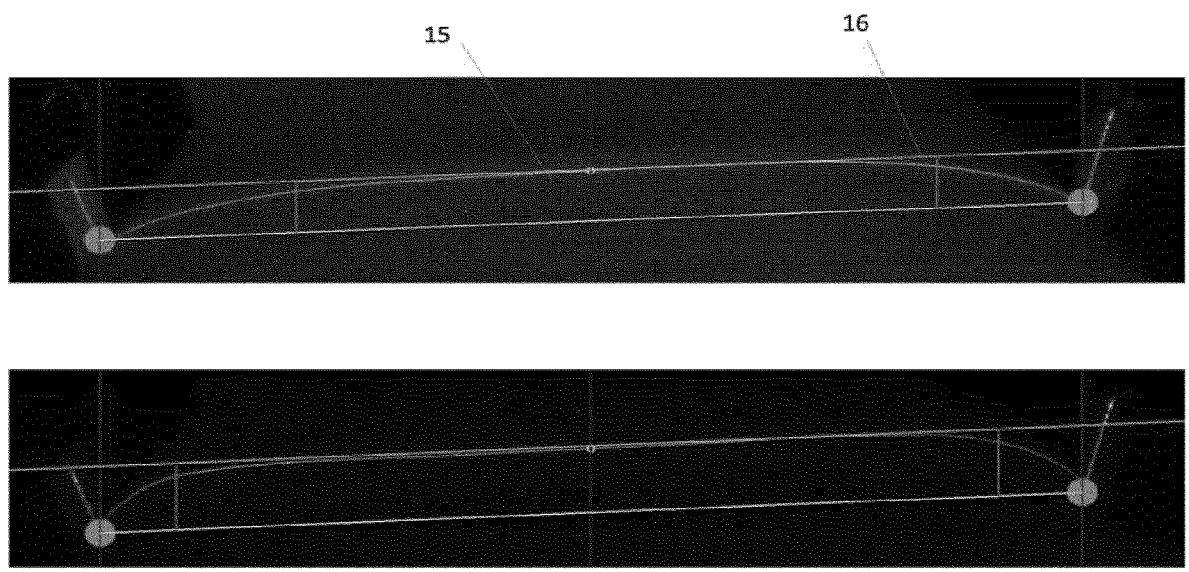
FIG. 5 is a further image of the projected laser line as seen by the camera.

Referring to FIG. 5, we see the laser lines examined on two mattresses with different constructions, top and bottom.

The top mattress has a canvas cover, and polyester wadding immediately beneath. These components have very little stretch, so the mattress has a pronounced hammock component.

The bottom mattress has cross-cut foam filling, with a stretchable jersey-knit cover, and therefore has less hammock component. The difference is evident in the spacing of the vertical lines 16. The top mattress has a longer span than the bottom mattress, as expected.

Also evident from the analyzed image is that the top mattress is firmer than the bottom mattress. This can be seen by the relatively small vertical displacement between the horizontal lines.

The resilience, viscoelastic, and other time-dependent properties of the mattress are also readily measured using this system. For example, as the apparatus is loaded onto the mattress, a succession of timed images can be captured, and all parameters previously mentioned may be plotted against time. Plotting displacement against time, the typical observation for a resilient mattress, such as a coiled spring mattress, would be an increasing displacement for a very brief period until full load was taken, followed by a flat line of constant displacement, with no further change. Conversely, a viscous mattress, such as memory foam, would exhibit a continued creep of displacement after full load was taken.

Numerous methods are available for characterizing or quantifying these properties. For example, a loading and unloading cycle could be used to establish a hysteresis loop, or creep between fixed time points under load could be used, or time constants post loading could be used to identify dynamic components.

In further embodiments, a plurality of laser lines may be used to project a grid, or an array of dots onto the surface of the mattress. This will allow the visualization and measurement of the deflection of the 2-dimensional surface, rather than a single line across the surface.

Further, the lower edges of the indenting masses may be arranged non-parallel, so that the spacing between them varies across the mattress surface.

It will be understood that the principles introduced by this invention as applicable to the characterization of mattress surfaces, are also applicable to the characterization of the elastic, viscoelastic, and tensile properties of other materials. This may include cushions such as wheelchair cushions or other seat cushions. It may also include biological materials, such as the human skin. For example, a very much smaller version of the device as described may be pressed into the skin of the foot to test for the reduction in surface elasticity which accompanies some medical conditions. Likewise, it may be used to measure the texture properties of a tumor. Likewise to measure the tone in muscle or other tissue, for example when monitoring contractions during labor.

It will of course be understood that various modifications and alterations are possible within the scope of the present invention as defined in the appended claims.

The invention claimed is:

1. A system for simultaneously measuring indentation hardness properties, span properties, and resilience properties of a mattress, comprising:
    a first indentation means and a second indentation means, each configured for being urged into the mattress with a predetermined force and causing an indentation in the mattress in a region of each of the first and second indention means and creating a curve on a surface of the mattress between the first indentation means and the second indentation means; and
    laser means for projecting a laser line onto the curve on the surface of the mattress spanning between the first indentation means and the second indentation means and configured for mapping an amplitude, shape, and time-dependency of resultant deflection of the surface of the mattress between the first indentation means and the second indentation means;
    wherein the span properties of the mattress are measured by determining a minimum distance away from the first indentation means or the second indentation means where there is no substantial indentation caused by either the first indentation means or the second indentation means; and
    wherein the laser means is configured for measuring a maximum amplitude of the curve on the surface of the mattress between the first indentation means and the second indentation means; and
    wherein the laser means is configured for capturing a succession of timed images as the first indentation means and the second indentation means are urged into the mattress.

2. A system as claimed in claim 1 wherein the mapping is carried out by photographic triangulation.

3. A system as claimed in claim 1 wherein the first and second indentation means are operable independently of each other.

4. A system as claimed in claim 1 wherein the first and second indentation means are operable together.

5. A system as claimed in claim 1 wherein the first and second indentation means are operable together and are rigidly connected together so as to facilitate simultaneous operation.

6. A system as claimed in claim 1 wherein lower edges of the first indentation means and the second indentation means are arranged non-parallel, so that spacing between them varies across the mattress surface.

7. A system as claimed in claim 1 wherein the laser means is configured to determine creep of the deflection of the surface of the mattress between the first indentation means and the second indentation means under a full load of the first indentation means and the second indentation means on the mattress using multiple timed images.

8. A system as claimed in claim 1 wherein the laser means is configured to measure time constants of deflection of the surface of the mattress after loading of the first indentation means and the second indentation means on the mattress using multiple timed images to identify dynamic components of properties of the mattress.

9. A system as claimed in claim 1 wherein the laser means is configured to use a loading and unloading cycle of the first indentation means and the second indentation means on the mattress to establish a hysteresis loop in deflection of the surface of the mattress using multiple timed images.

10. A system as claimed in claim 1 wherein the laser means is configured to project a plurality of laser lines to project a grid onto the surface of the mattress.

11. A system for simultaneously measuring indentation hardness properties, span properties, and resilience properties of a mattress, comprising:
    an indentation assembly comprising first and second masses connected together by a rigid member;
    a vertical member connected to the indentation assembly, the vertical member capable of being raised or lowered to raise or lower the indentation assembly;
    a horizontal member connected to the vertical member;
    a laser apparatus configured to emit a laser line, the laser apparatus being mounted to the horizontal member and positioned so that the laser line is projected to span between the first and second masses; and
    a camera mounted to the horizontal member in a position that is horizontally offset from the laser line emitted by the laser, thereby permitting visualization by oblique triangulation of a distance of a surface on which the laser line is projected;
    wherein the first and second masses of the indentation assembly are configured to be urged into the mattress with a predetermined force to thereby cause an indentation in the mattress in a region of each of the first and second masses and create a curve of the laser line on a surface of the mattress between the first and second masses corresponding to a deformed shape of the mattress between the first and second masses;
    wherein the camera is configured to capture a succession of timed images as the first and second masses are urged into the mattress;
    wherein the camera is configured to capture images of the laser line on the surface of the mattress between the first and second masses, such that an amplitude, shape, and time-dependency of the curve of the laser line on the surface of the mattress between the first and second masses can be mapped, and a maximum amplitude of the curve of the laser line on the surface of the mattress between the first and second masses can be measured; and wherein the span properties of the mattress are measured by determining a minimum distance away from the first mass or the second mass where there is no substantial indentation caused by either the first mass or the second mass.

12. A system as claimed in claim 11 wherein the indentation assembly is configured to be lowered onto the mattress under its own weight to cause indentation of the first and second masses into the mattress under load.

13. A system as claimed in claim 11 wherein the indentation assembly is configured to be driven into the mattress by an actuator until a prescribed load or a prescribed deformation by the first and second masses into the mattress is achieved.

14. A system as claimed in claim 11 wherein lower edges of the first and second masses are flat and are arranged parallel to each other.

15. A system as claimed in claim 11 wherein lower edges of the first and second masses are arranged non-parallel to each other, so that spacing between them varies across the mattress surface.

16. A system as claimed in claim 11 further comprising a hoisting apparatus operable to raise and lower the indentation assembly relative to the mattress.

17. A system as claimed in claim 11 wherein the multiple timed images captured by the camera include images from which creep of the deflection of the surface of the mattress between the first and second masses under a full load of the first and second masses on the mattress can be determined.

18. A system as claimed in claim 11 wherein the multiple timed images captured by the camera include images from which time constants of deflection of the surface of the mattress after loading of the first and second masses on the mattress can be measured to identify dynamic components of properties of the mattress.

19. A system as claimed in claim 11 wherein the multiple timed images captured by the camera include images from which a loading and unloading cycle of the first and second masses can be used to establish a hysteresis loop in deflection of the surface of the mattress.

* * * * *